United States Patent [19]
Chiyoda et al.

[11] Patent Number: 4,463,199
[45] Date of Patent: Jul. 31, 1984

[54] METHOD FOR PRODUCING PHLOROGLUCIN

[75] Inventors: Tsutomu Chiyoda, Toyonaka; Makoto Nakamura, Ibaraki; Shinichi Hasegawa, Otsu, all of Japan

[73] Assignee: Sumitomo Chemical Company, Limited, Osaka, Japan

[21] Appl. No.: 443,692

[22] Filed: Nov. 22, 1982

[30] Foreign Application Priority Data

Dec. 1, 1981 [JP] Japan .................................. 56-193939

[51] Int. Cl.$^3$ ............................................. C07C 37/08
[52] U.S. Cl. ................................... 568/768; 568/754; 568/763; 568/798
[58] Field of Search ............... 568/768, 749, 753, 754, 568/798, 763

[56] References Cited

FOREIGN PATENT DOCUMENTS 12239  4/1955  German Democratic Rep. ..................................... 568/768
751598 6/1956  United Kingdom ................ 568/768

Primary Examiner—Werren B. Lone
Attorney, Agent, or Firm—Stevens, Davis, Miller & Mosher

[57] ABSTRACT

In a method for producing phloroglucin by a decomposition of 1,3,5-triisopropylbenzene trihydroperoxide (hereinafter referred to as THPO), a method for producing phloroglucin wherein an acid catalytic decomposition is carried out under the condition that:

(1) at least one member selected from the group consisting of perchloric acid, sulfuric anhydride and boron trifluoride be used as a catalyst,
(2) the amount of the catalyst above in the reaction solution be 1 to 100 ppm,
(3) the water content in the reaction solution be not more than 2% by weight, and
(4) the total amount of the carbinol group of carbinols (having a structure in which part or all of the three hydroperoxy groups of THPO have been replaced by hydroxyl groups) contaminating the raw material for reaction be not more than 1/5 equivalent based on THPO.

The phloroglucin is useful as a starting material of medicines and photosensitizers.

1 Claim, No Drawings

METHOD FOR PRODUCING PHLOROGLUCIN

The present invention relates to a method for producing phloroglucin in high yields by the decomposition of 1,3,5-triisopropylbenzene trihydroperoxide (hereinafter referred to as THPO).

Production of phloroglucin by the decomposition of THPO is well known as described also in East German Pat. No. 12,239/1955 and British Pat. No. 751,598. These well-known methods, however, use hydrochloric acid, sulfuric acid, etc. as catalyst, and yet the amount of the catalyst is as extremely large as amounts approximately equal to the reaction solution. Consequently, there was a problem that side reactions are caused and also the yield is as very low as about 50%.

For this reason, the present inventors extensively studied to produce phloroglucin in high yields by inhibiting side reactions on the decomposition of THPO, and as a result, found that the kind and amount of catalyst used, the water content in the reaction system and the amount of carbinols exert a very serious effect in said decomposition, and that the objects described above can not be achieved until these factors are satisfied under specified conditions. The present invention was completed based on this finding. According to the present invention, the following method is provided: In a method for producing phloroglucin by a decomposition of 1,3,5-triisopropylbenzene trihydroperoxide (hereinafter referred to as THPO), a method for producing phloroglucin wherein an acid catalytic decomposition is carried out under the condition that:

(1) at least one member selected from the group consisting of perchloric acid, sulfuric anhydride and boron trifluoride be used as a catalyst,
(2) the amount of the catalyst above in the reaction solution be 1 to 100 ppm,
(3) the water content in the reaction solution be not more than 2% by weight, and
(4) the total amount of the carbinol group of carbinols (having a structure in which part or all of the three hydroperoxy groups of THPO have been replaced by hydroxyl groups) contaminating the raw material for reaction be not more than 1/5 equivalent based on THPO.

In the reaction of the present invention, it is necessary that at least one member selected from the group consisting of perchloric acid, sulfane and boron trifluoride is used as catalyst, and the amount of the catalyst in the reaction solution is 1 to 100 ppm, preferably 2 to 30 ppm.

When sulfuric acid, hydrochloric acid or toluenesulfonic acid generally well known as an acid catalyst is used, the rate of decomposition is extremely slow with such trace amounts as specified in the present invention. While when large quantities of the acid are used so as to allow the decomposition to proceed smoothly, side reactions such as acetylation, conversion to tarry matters, etc. are caused to lower the decomposition yield.

In the reaction of the present invention, the amount of catalyst used is as described above, but when it is below this range, the progress of the reaction is slow, while when it exceeds this range, side reactions are promoted, either of the both cases being therefore undesirable.

Also, in this reaction, there is a close relation between the water content and the catalyst amount contained in the reaction system. For example, when the water content is increased, the decomposition becomes markedly slow unless the catalyst amount is increased. Such increase in the catalyst amount causes the promotion of side reactions as described above, thereby leading to a reduction in yield. For this reason, the water content in this reaction system needs to be not more than 2% by weight, preferably not more than 1% by weight.

Also, in the reaction of the present invention, it is necessary that the total amount of the carbinol group of carbinols contaminating the raw material for reaction applied to the decomposition is not more than 1/5 equivalent based on THPO.

Hereupon, the term "carbinols" means a compound having a structure in which part or all of the three hydroperoxy groups of THPO have been replaced by hydroxyl groups.

Generally, in synthesizing hydroperoxide by the auto-oxidation of alkylbenzenes, a carbinol compound is produced as by-product, and it is well known that this carbinol compound forms dehydration-condensates with phenols in acid decomposition, thereby markedly lowering the decomposition yield. In the decomposition of THPO, contamination with carbinols similarly causes a marked reduction in yield, so that carbinols need to be previously removed as much as possible.

Complete separation of carbinols from THPO, however, requires a very complicated treatment, and therefore, it is substantially almost impossible to carry out economically on the industrial scale.

The present inventors made an extensive study on a relation between the amount of carbinols based on THPO and the decomposition yield, and found the followings: The effect of carbinols on the decomposition yield is not always proportional to the amount of carbinols as contaminant; and when the total amount of the carbinol group of carbinols present in the raw material for reaction is below a border line at which said total amount is 1/5 equivalent based on THPO, said effect is of such a degree that the decomposition yield slowly lowers with an increase in the amount of carbinols to show no sudden change, but when said total amount exceeds the border line, the decomposition yield suddenly lowers with an increase in the amount of carbinols. Based on this novel finding, it is necessary that, in order to inhibit side reactions and to improve the decomposition yield in the method of the present invention, the content of carbinols is not more than the above-mentioned amount specified by the present invention.

Thus, according to the method of the present invention, phloroglucin can be produced in good yields and good efficiency be decomposing THPO under conditions wherein the kind and amount of catalyst, water content and carbinols content are each specified by the present invention.

Next, the present invention will be illustrated with reference to the following examples. Hereupon, carbinols described in the examples were expressed for convenience as converted to 1,3-di-(2-hydroperoxy-2-propyl)-5-(2-hydroxy-2-propyl)benzene (hereinafter, abbreviated as MCDH) (MW=284).

EXAMPLE 1

To a 2-liter glass reactor equipped with a stirrer was added 150 g of a 5 ppm perchloric acid/acetone solution which was then kept at 58° to 62° C. with stirring.

1000 Grams of a raw material for decomposition shown in the table below and 52.6 g of a 0.01 wt.% perchloric acid/methyl isobutyl ketone (MIBK) solution were added dropwise at the same time while maintaining the decomposition temperature at 58° to 62° C., thereby carrying out decomposition (perchloric acid concentration in the reaction solution, 5 ppm).

After beginning of the dropwise addition, the decomposition solution was slowly colored from yellow to pale yellowish red, and it turned pale red at the end of the dropwise addition. After 35 minutes including a time required for the dropwise addition, the hydroperoxy concentration in the reaction solution became not more than 0.05 wt.% to rapidly complete the decomposition.

After completion of the decomposition, the amount of the decomposition solution was 1200.6 g, the phloroglucin concentration in the solution was 4.82 wt.%, and the decomposition yield was 92.0%.

| Composition of raw material for decomposition (wt. %) | | | |
|---|---|---|---|
| THPO | MCDH | Water | MIBK |
| 15.0 | 1.6 | 0.1 | 83.3 |

EXAMPLE 2

Decomposition was carried out in the same manner as in Example 1 except that the perchloric acid concentrations of the perchloric acid/acetone solution and perchloric acid/MIBK solution on feeding were adjusted so that the perchloric acid concentration in the decomposition solution was 50, 100, 500 and 1000 ppm, respectively.

With an increase in the acid concentration, coloration of the decomposition solution became remarkable, and in the case of 1000 ppm addition, the decomposition solution after completion of decomposition colored dark red. The decomposition yields in the respective decompositions were as shown in the table below.

|  | Perchloric acid (ppm) | Yield (%) |
|---|---|---|
| Example | 50 | 91 |
|  | 100 | 90 |
| Comparative example | 500 | 75 |
|  | 1000 | 65 |

EXAMPLE 3

Decomposition was carried out in the same manner as in Example 1 except that the acid catalyst was replaced by sulfuric anhydride, boron trifluoride, sulfuric acid or toluenesulfonic acid. When sulfuric acid or toluenesulfonic acid was used, the decomposition was insufficient even after the lapse of 10 hours, so that the decomposition was carried out with an increased amount of 500 ppm.

|  | Acid catalyst | Concentration (ppm) | Yield (%) |
|---|---|---|---|
| Example | Sulfuric anhydride | 5 | 90 |
|  | Boron trifluoride | 5 | 92 |
| Comparative example | Sulfuric acid | 500 | 65 |
|  | Toluenesulfonic acid | 500 | 63 |

EXAMPLE 4

Decomposition was carried out in the same manner as in Example 1 except that the water content in the raw material for decomposition was adjusted with water so that it was 0.5, 1.0, 2.0 and 4.0 wt.%. The results are shown in the table below.

|  | Water (wt. %) | Acid catalyst (wt. %) | Yield (%) |
|---|---|---|---|
| Example | 0.5 | 10 | 92 |
|  | 1.0 | 60 | 91 |
| Comparative example | 2.0 | 200 | 83 |
|  | 4.0 | 1000 | 70 |

EXAMPLE 5

Decomposition was carried out in the same manner as in Example 1 except that the MCDH content in the raw material for decomposition was adjusted with addition of MCDH so that it was 2.4, 3.2, 4.8 and 8.0 wt.%, and besides that the amount of acid catalyst added was made 10 ppm, taking into account that the water content in the reaction solution increases when condensates with carbinols were formed. The results are shown in the table below.

|  | MCDH content (wt. %) | Equivalent of carbinol group*[1] | Yield (%) |
|---|---|---|---|
| Example | 2.4 | 0.15 | 91 |
|  | 3.2 | 0.20 | 90 |
| Comparative example | 4.8 | 0.30 | 85 |
|  | 8.0 | 0.50 | 60 |

*[1]Value based on THPO.

REFERENCE EXAMPLE 1

The decomposition solution obtained in Example 1 was neutralized with sodium carbonate and concentrated to 300 g, and parts of acetone and MIBK were removed by evaporation.

Thereafter, 450 g of water was added to the concentrated solution, and the pH of the solution was adjusted to 9 with a conc. aqueous caustic soda with stirring to extract a greater part of phloroglucin with the aqueous layer. After liquid/liquid separation, 130 g of fresh MIBK was added to the aqueous layer to extract impurities with the MIBK layer, and the aqueous layer was acidified with sulfuric acid and cooled to 15° C. to deposit crystals. The deposited pale yellow crystal of phloroglucin was filtered off.

Activated carbon was added to the resulting phloroglucin crystal which was then recrystallized from water, filtered off and dried to obtain about 47 g of anhydrous phloroglucin as white crystal.

Thereafter, phloroglucin obtained from the MIBK layer after extraction and the filtrate after recrystallization was recycled to the concentrated solution to carry out purification similarly. Thus, about 52 g of anhydrous phloroglucin was obtained as white crystal on and after the second operation.

Purity, not less than 98%; m.p., 217°–219° C.; purification yield, 90%; and overall yield of from decomposition to purification, about 83%.

What is claimed is:

1. In the method for producing phloroglucin by decomposition of 1,3,5-triisopropylbenzene trihydroperoxide (hereinafter referred to as THPO) in the presence of an acid catalyst at conventional temperatures, the improvement comprising carrying out the method under conditions wherein:

(1) at least one member selected from the group consisting of perchloric acid, sulfuric anhydride and boron trifluoride is used as the catalyst, (2) the amount of the catalyst above in the reaction solution is 1 to 100 ppm, (3) the water content in the reaction is not more than 2% by weight, and (4) the total amount of the carbinol group of carbinols (having a structure in which part or all of the three hydroperoxy groups of THPO have been replaced by hydroxyl groups) contaminating the raw material for reaction is not more than 1/5 equivalent based on THPO.

* * * * *